United States Patent
Kwun et al.

(10) Patent No.: US 6,205,859 B1
(45) Date of Patent: Mar. 27, 2001

(54) METHOD FOR IMPROVING DEFECT DETECTABILITY WITH MAGNETOSTRICTIVE SENSORS FOR PIPING INSPECTION

(75) Inventors: Hegeon Kwun; Keith A. Bartels, both of San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 09/228,456

(22) Filed: Jan. 11, 1999

(51) Int. Cl.[7] .................................................. G01N 29/12
(52) U.S. Cl. ................................................. 73/579; 73/602
(58) Field of Search ............................. 73/579, 602, 620, 73/622, 627, 629, 630

(56) References Cited

U.S. PATENT DOCUMENTS

| | | | |
|---|---|---|---|
| 3,776,026 | * 12/1973 | Adler et al. | 73/602 |
| 4,393,711 | * 7/1983 | Lapides | 73/592 |
| 4,428,235 | * 1/1984 | Sugiyama | 73/579 |
| 4,428,237 | * 1/1984 | Zeger et al. | 73/592 |
| 4,545,250 | * 10/1985 | Miwa | 73/602 |
| 4,759,221 | * 7/1988 | Ortlieb et al. | 73/627 |
| 5,195,046 | 3/1993 | Gerardi et al. | 364/506 |
| 5,216,921 | * 6/1993 | Tsuboi | 73/579 |
| 5,439,157 | 8/1995 | Geier et al. | 228/9 |
| 5,469,060 | 11/1995 | Meyerand | 324/309 |
| 5,526,689 | 6/1996 | Coulter et al. | 73/592 |
| 5,574,639 | 11/1996 | Qian et al. | 364/724.01 |
| 5,581,037 | * 12/1996 | Kwun et al. | 73/623 |
| 5,612,495 | 3/1997 | Shimada et al. | 73/579 |
| 5,665,913 | 9/1997 | Chung | 73/583 |
| 5,719,791 | 2/1998 | Neumeier et al. | 364/574 |
| 5,955,669 | * 9/1999 | Egami | 73/579 |

* cited by examiner

Primary Examiner—Hezron Williams
Assistant Examiner—Rose M. Miller
(74) Attorney, Agent, or Firm—Cox & Smith Incorporated

(57) ABSTRACT

An improved method for defect detection with systems using magnetostrictive sensor techniques. The improved method involves exciting the magnetostrictive sensor transmitter by using a relatively broadband signal instead of a narrow band signal typically employed in existing procedures in order to avoid signal dispersion effects. The signal detected by the magnetostrictive sensor receiver is amplified with an equally broadband signal amplifier. The amplified signal is transformed using a time-frequency transformation technique such as a short-time Fourier transform. Finally, the signal characteristics associated with defects and anomalies of interest are distinguished from extraneous signal components associated with known wave propagation characteristics. The process of distinguishing defects is accomplished by identifying patterns in the transformed data that are specifically oriented with respect to the frequency axis for the plotted signal data. These identified patterns correspond to signals from either defects or from known geometric features in the pipe such as welds or junctions. The method takes advantage of a priori knowledge of detected signal characteristics associated with other wave modes (such as flexural waves) and sensor excitation as well the effects caused by liquid induced dispersion.

10 Claims, 4 Drawing Sheets

METHOD FOR IMPROVING DEFECT DETECTABILITY WITH MAGNETOSTRICTIVE SENSORS FOR PIPING INSPECTION

BACKGROUND OF THE INVENTION

1. Field of the Invention

The present invention relates generally to methods for the Non-Destructive Evaluation (NDE) of pipes and tubes using magnetostrictive sensor technologies. The present invention relates more specifically to an improved method for detecting defects in the signal analysis process associated with the use of magnetostrictive sensor technologies for the inspection of pipes and tubes.

2. Description of the Related Art

Magnetostrictive sensor technologies have been used successfully for a period of time with the inspection of pipes and tubes in processing plants such as refineries, chemical plants, steam process plants and the like. Examples of the use of magnetostrictive sensors, and the various analytical techniques associated therewith, are disclosed in U.S. Pat. Nos. 5,456,113 and 5,457,994, each entitled Non-Destructive Evaluation of Steel Cables and Ropes Using Magnetostrictively Induced Ultrasonic Waves and Magnetostrictively Detected Acoustic Emissions, as well as U.S. Pat. No. 5,581,037 entitled Non-Destructive Evaluation of Pipes and Tubes Using Magnetostrictive Sensors, all of which are commonly owned by the assignee of the present invention, Southwest Research Institute.

The techniques associated with such NDE inspections of pipes, tubes, cables and the like typically involve generating longitudinal waves along the length of the pipe or tube and analyzing signals that are reflected from defects and anomalies within the pipe or tube. One of the many advantages of this technique is the ability to detect defects by sensing the reflected signal at the same physical location at which the interrogating signal waves are generated.

Because mechanical waves generated by magnetostrictive sensors can propagate a long distance along a structure under inspection the techniques are capable of inspecting very long or large segments, typically more than a hundred feet under favorable conditions, of pipe very rapidly. These techniques also provide a complete volumetric inspection of a long section of pipe with minimum ancillary activity such as surface preparation, scaffolding or insulation removal. These magnetostrictive sensor methods therefore offer a very efficient and comprehensive mechanism for pipe and tube inspection.

In general, the longitudinal wave modes utilized in the above referenced techniques for inspection are dispersive in nature. This means that the velocity of the mechanical wave propagation varies with the wave frequency. FIG. 1 provides a illustrative example of the dispersion curves for the first two longitudinal wave modes, L(0,1) and L(0,2), which are typically used with the above referenced magnetostrictive sensor techniques. To simplify the detection of defects within the reflected signal pattern, the techniques described above utilize the waves in the frequency region where the dispersion curve is relatively flat ($V_o$ and $V_p$) and avoid those regions ($V_o/2\pi b$ and $KV_p/2\pi b$) where the dispersion curve changes rapidly with frequency. In order to confine the bandwidth of the wave pulse within the desired frequency range, and thus avoid excessive dispersion effects, a relatively narrow band excitation signal is used for transmitting the interrogating waves into the pipe structure. A tonal burst consisting of several cycles of sinusoidal wave at a specific wave frequency have been typically employed for this purpose. The effectiveness of magnetostrictive sensor techniques along these lines has been well proven in operating processing plants.

It has been recognized, however, that positive discrimination and identification of defect signals within the overall detected signal can sometimes be difficult due to the presence of extraneous signals not associated with defects and anomalies. These extraneous signals include those of other wave modes (mostly flexural) that might be produced in the pipe wall due to non-symmetric material properties and sensor excitation. In addition, for situations where the pipe or tube is liquid filled, extraneous signals can be caused by liquid induced dispersion effects. These extraneous signals may be confused as defect reflections or may mask or radically alter defect signals present in the detected signals.

Examples of previous attempts in the prior art to improve the defect detectability of NDE sensors include the following patents:

U.S. Pat. No. 5,612,495 issued to Shimada et al. on Mar. 18, 1997, entitled Non-Destructive Examination Device, describes a system that uses magnetostrictive transmitters and response sensors to carry out the non-destructive evaluation of a material. The system anticipates the use of a resonant frequency for the interrogating signal. The signal processing methods are described as potentially including a high speed Fourier transformation process or an integral process. No specific characterization or selection of the best or most appropriate signal processing method is made.

U.S. Pat. No. 5,526,689 issued to Coulter et al. on Jun. 18, 1996, entitled Acoustic Emission for Detection of Corrosion Under Insulation, describes a method and apparatus for detecting the presence of surface corrosion under insulation on a pipe structure. This patent anticipates the use of a broadband of acoustic waves to interrogate the structure. The sound waves are detected by piezoelectric sensors and converted to electrical signals for processing. The signal analysis method in Coulter et al. involves producing RMS voltage signals indicative of the detected sound waves and comparing the RMS voltage signals to standard signals obtained from uncorroded piping. The analysis involves a strict amplitude comparison to distinguish the signal component from the defect.

U.S. Pat. No. 5,195,046 issued to Gerardi et al. on Mar. 16, 1993, entitled Method and Apparatus for Structural Integrity Monitoring, describes a piezoelectric transducer based system designed for the detection, monitoring, and analysis of such things as aircraft structures. The system utilizes vibration signatures and recognizes changes in the vibration signatures as indicative of faults, cracks, deteriorations, etc. Various pattern recognition techniques are utilized. Data acquisition is accomplished using piezoelectric sensors and is digitized before being converted to the frequency domain via a fast Fourier transform. Time and/or frequency domain signatures are used in the signature pattern analysis. The patent lists 25 illustrative features (column 11) that include both time and frequency domain parameters as providing the basis for pattern recognition.

U.S. Pat. No. 5,665,913 issued to Chung on Sep. 9, 1997, entitled Method and Apparatus for Evaluation and Inspection of Composite-Repaired Structures, describes a system and method for NDE of composite-repaired structures wherein the signal transmitters and sensors are piezoelectric based devices. Analysis is carried out by comparing an output signal to a baseline reference signal generated at the time of composite repair. The signal processor involved in Chung includes an isolation filter, an amplifier, and a frequency domain integrator. The system anticipates the use of either a single frequency for interrogating the material or a range of frequencies.

U.S. Pat. No. 5,469,060 issued to Meyerand on Nov. 21, 1995 entitled Time Encoded Magnetic Resonance Imaging, describes a system that utilizes a separate set of signal transducers and applies a resonant frequency pulse to the material under investigation. The RF signals received as a function of time are converted to a set of frequency domain functions at specific times relating to specific strips in the image being generated. The frequency domain functions in the form of strips are combined sequentially to form the entire time frequency domain function image.

U.S. Pat. No. 5,719,791 issued to Neumeier et al. on Feb. 17, 1998, entitled Methods, Apparatus and Systems for Real Time Identification and Control of Modes of Oscillation, describes various methods for signal identification within a noisy background. The Neumeier et al. patent describes a system for controlling vibrations and oscillations with real time detection and compensation through an actuator. Various time frequency functions are applied to the signal for analysis.

U.S. Pat. No. 5,574,639 issued to Qian et al. on Nov. 12, 1996, entitled System and Method for Constructing Filters for Detecting Signals Whose Frequency Content Varies With Time, is generally directed to a signal analysis method intended to reliably detect the presence of signals of interest, especially those whose frequency content varies with time. The Qian et al. invention is directed to the development and use of time templates designed to match the received signal of interest. The patent describes its application as including any situation where a signal travels through media and wherein the media transforms or disperses the signal into a signal whose frequency content varies with time. The patent applies what is referred to as the Gabor Spectrogram to a computer representation of the signals in the joint time-frequency domain for the purpose for instantaneous frequency estimation. The patent distinguishes STFT as not being the ideal representation for tracking the parameters of concern.

U.S. Pat. No. 5,439,157 issued to Geier et al. on Aug. 8, 1995, entitled Automated Butt Weld Inspection System, describes an electromagnetic acoustic transducer (EMAT) based system that produces an ultrasonic shear wave in a material containing welds and the like. A second EMAT receives the reflected shear wave.

None of the above described methods and systems, however, have been able to adequately distinguish signal characteristics that derive from extraneous features of no interest from those signal components that derive from the types of defects and anomalies of interest in a damage, deterioration, or corrosion study. The signal analysis techniques utilized thus far are generally incapable of distinguishing a time, frequency and amplitude signal component associated with a defect of interest from similar time, frequency and amplitude signal components associated with geometric and/or otherwise non-relevant causes.

It would be desirable to have an NDE system for pipe and/or tube inspection that utilizes magnetostrictive sensor techniques and is capable of analyzing a detected signal in a manner that permits the discrimination of extraneous signal components not representative of defects or anomalies of interest. It would be desirable if such a system could be automated to the extent that rapid discrimination of such signal components not representative of defects or anomalies of interest, would provide an accurate and rapid identification of the location and nature of defects and anomalies of interest.

SUMMARY OF THE INVENTION

It is therefore an object of the present invention to provide a method for improved defect detectability utilizing magnetostrictive sensor technologies for pipe and tube inspection.

It is another object of the present invention to provide a method for improved defect detectability using magnetostrictive sensor technologies for pipe and/or tube inspection that permits the discrimination of signal components indicative of extraneous factors unassociated with defects and anomalies of interest.

It is another object of the present invention to provide an improved method for defect detectability using magnetostrictive sensor technologies for pipe and/or tube inspection that provides rapid detection and discrimination of signal components not associated with defects and anomalies of interest, based upon a priori knowledge of signal characteristics caused by extraneous factors within the geometry and environment of the pipes and tubes under inspection.

It is another object of the present invention to provide a method for improved defect detectability using magnetostrictive sensor technologies for piping inspection that provides analysis techniques capable of automation to extent that signal characteristics associated with extraneous factors may be rapidly identified and distinguished, thereby permitting the rapid identification and quantification of signal characteristics associated with defects and anomalies of interest.

In fulfillment of these and other objectives, the present invention provides an improved method for defect detection with systems using magnetostrictive sensor techniques. The improved method involves exciting the magnetostrictive sensor transmitter by using a relatively broadband signal instead of a narrow band signal typically employed in existing procedures in order to avoid signal dispersion effects. The signal detected by the magnetostrictive sensor receiver is amplified with an equally broadband signal amplifier. The amplified signal is transformed using a time-frequency transformation technique such as a short-time Fourier transform. Finally, the signal characteristics associated with defects and anomalies of interest are distinguished from extraneous signal components associated with known wave propagation characteristics. The process of distinguishing defects is accomplished by identifying patterns in the transformed data that are specifically oriented with respect to the frequency axis for the plotted signal data. These identified patterns correspond to signals from either defects or from known geometric features in the pipe such as welds or junctions. The method takes advantage of a priori knowledge of detected signal characteristics associated with other wave modes (such as flexural waves) and sensor excitation as well the effects caused by liquid induced dispersion.

BRIEF DESCRIPTION OF THE DRAWINGS

FIG. 2b is a graphical representation of a detected signal from the apparatus shown in FIG. 2a.

DESCRIPTION OF THE PREFERRED EMBODIMENT

Figure 1:
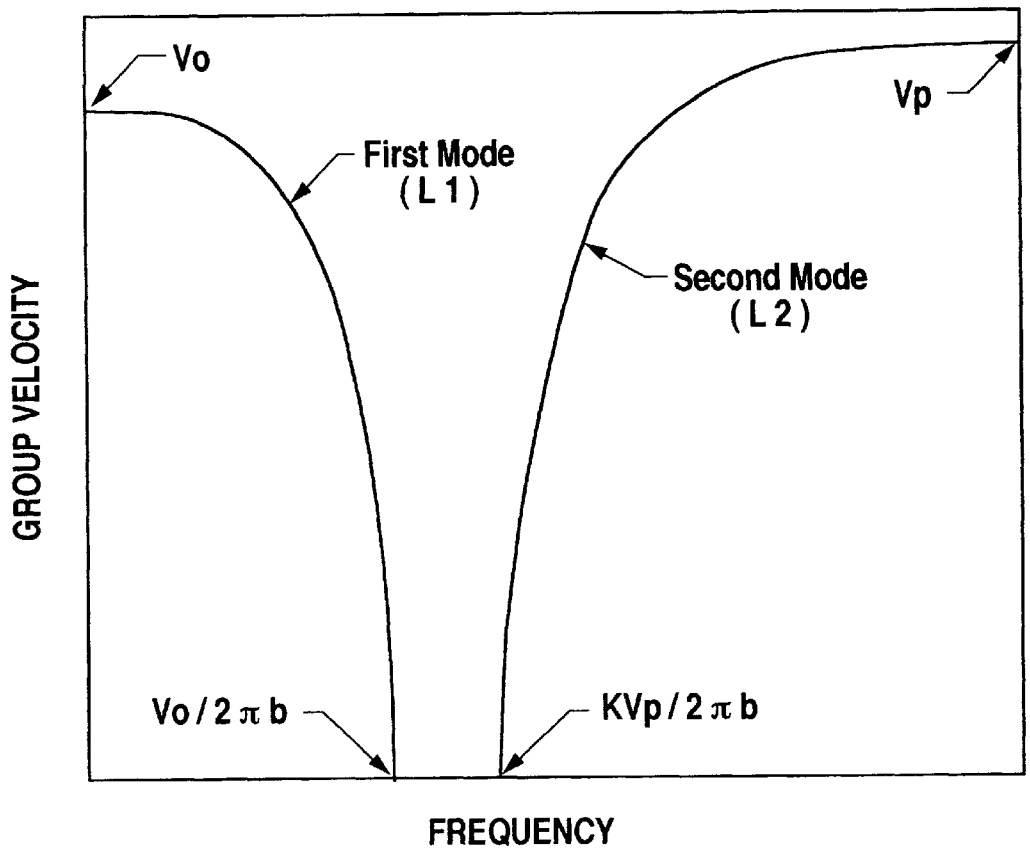
FIG. 1 is a graphical representation of dispersion curves for the first two longitudinal wave modes L(0,1) and L(0,2), typically used with magnetostrictive sensor based NDE techniques.

Reference is again made to FIG. 1 for a brief description of the basic behavior of the longitudinal wave modes used with both the interrogating signal and the detected signal as typically experienced in conjunction with magnetostrictive sensor NDE techniques. As indicated above the NDE inspection of pipes, tubes, cables and the like utilizing magnetostrictive sensors, typically involves generating longitudinal waves along the length of the pipe or tube and analyzing the signals that are reflected from defects and anomalies within the pipe or tube. The longitudinal wave modes utilized are dispersive in nature as is evidenced by the graph shown in FIG. 1. In FIG. 1 the first two longitudinal wave modes L(0,1) and L(0,2) exhibit significant dispersive effects within certain regions of the frequency spectrum. While this dispersive effect is helpful under some signal analysis techniques, it is generally considered a characteristic to be avoided when trying to isolate changes in the signal brought about by defects and anomalies of interest.

Again as indicated above, magnetostrictive sensor techniques have generally relied on the use of an interrogating signal confined to a narrow frequency bandwidth in order to avoid those portions of the frequency spectrum that exhibit excessive dispersion effects. While this process of selecting a narrow bandwidth eliminates detected signal features that derive from the dispersion of the longitudinal waves, it does not begin to address many of the other signal characteristics that result from factors in the inspection environment unassociated with defects and anomalies of interest. Such factors include the geometric features of the object under inspection as well as the dispersive effects of other wave modes and the dispersive effects brought about by a liquid that might be present in the pipe or tube. The present invention therefore addresses the problem of identifying these additional extraneous signal characteristics and distinguishes them from those signal characteristics which derive from features of interest.

Figure 2A:
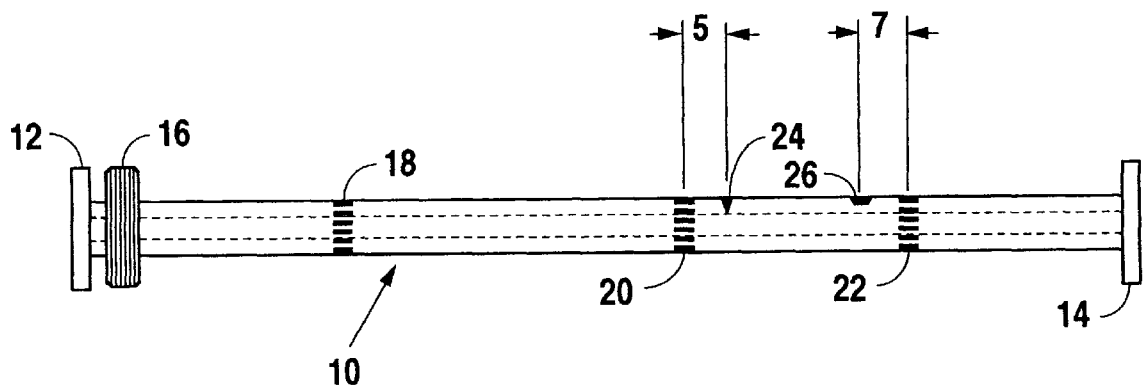
FIG. 2a is a schematic diagram showing a test apparatus appropriate for implementation of the methods of the present invention.
Figure 2B:
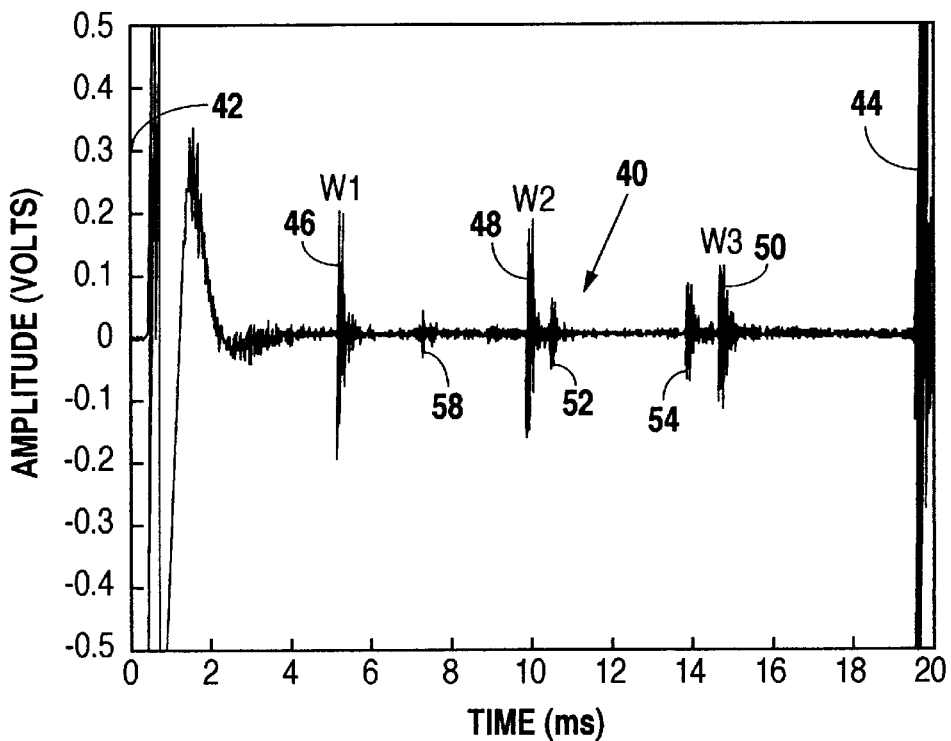
Figure 4:
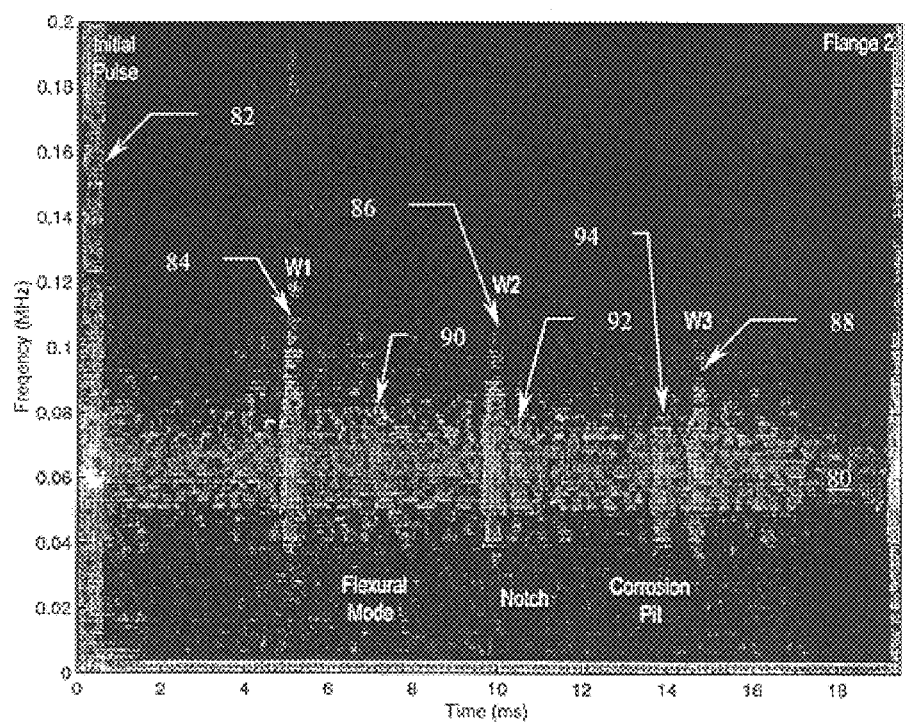
FIG. 4 is a graphical representation of the time evolution of each frequency component of the detected signals shown in FIG. 2 after implementation of a short-time Fourier transform to the data.

Reference is made to FIG. 2a for a brief description of a typical test structure appropriate for implementation of the method of the present invention and which structure provides the environment for the generation of the signals shown in FIG. 2b and FIG. 4. FIG. 2a discloses a test setup comprising a length of pipe under inspection. In FIG. 2a, pipe section (10) terminates on each end with flange sections (12) and (14). Between flange sections (12) and (14) are three typical girth weld joints (18), (20), and (22). At a first accessible end of pipe section (10) adjacent to flange (12) is magnetostrictive sensor (16). In the preferred embodiment, and the test apparatus utilized to generate the signals described herein, magnetostrictive sensor (16) is comprised of components well known in the art for both generating an interrogating signal and receiving a reflected signal back for analysis.

In addition two (2) anomalies of interest are artificially incorporated into the structure of pipe section (10) as notch (24) and corrosion pit (26). This test set up therefore provides a number of features anticipated to cause signal characteristics that are representative of defects and anomalies of interest or are representative of features that could easily be confused with such defects and anomalies of interest.

The test setup includes a pipe section (10) that is 168 feet long, with a 4.5 inch outside diameter, and a 0.337 inch thick wall. As indicated above, magnetostrictive sensor (16) is placed near flange (12) at one end of pipe section (10). The interrogating signal generated by magnetostrictive sensor (16) is expected to encounter girth welds (18), (20), and (22) as well as the defects represented by notch (24) and corrosion pit (26). In the test set up shown in FIG. 2a, notch (24) is spaced from girth weld (20) by a distance of five (5) feet. Corrosion pit (26) is spaced from girth weld (22) by a distance of seven (7) feet.

FIG. 2b discloses as a first example, a detected signal from the test setup shown in FIG. 2a. Signal components indicative of the various geometric structures shown in the test setup of FIG. 2a are each identifiable in FIG. 2b. Specifically, initial pulse (42) is followed after a period of time by signal component (46) representative of girth weld (18). Girth weld (20) generates signal component (48) which is quickly followed by signal component (52), representative of notch (24). Corrosion pit (26) returns signal component (54) which is quickly followed by signal component (50), representative of girth weld (22). Finally, signal (40) completes its path down the length of pipe section (10) by returning signal component (44), representative of flange (14).

In addition to the easily identifiable signal components described above, an extraneous signal component (58) is disclosed midway between signal components (46) and (48). This extraneous signal component (58) could be falsely identified as a defect in the pipe section positioned somewhere between girth welds (18) and (20). The interpretation of signal (40) shown in FIG. 2b in this manner would lead to further mechanical and visual inspections of the appropriate portion of pipe section (10) believed to have caused the extraneous signal component if no additional means were available to differentiate the signal component. Experience has shown that such extraneous signal components are often the result of non-defect factors which, given the appropriate signal analysis techniques of the present invention, could have been discriminated prior to the effort and expense of additional pipe inspection.

Figure 3:
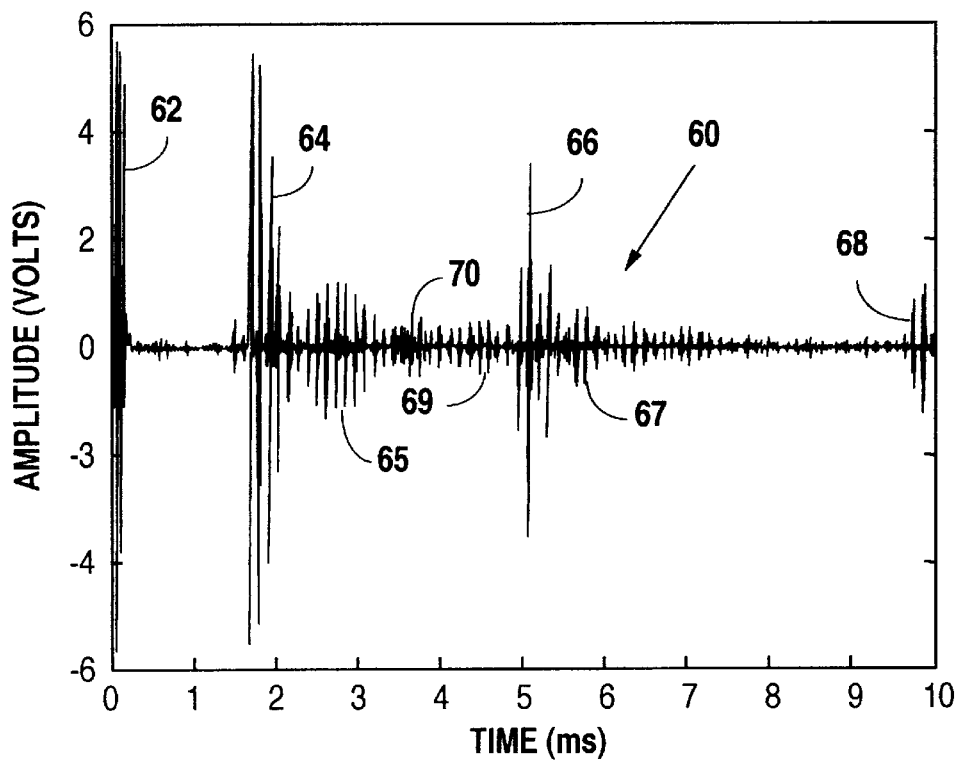
FIG. 3 is a second graphical representation of a detected signal using magnetostrictive sensor techniques.

FIG. 3 represents signal data obtained from an operational 6–5/8 inch outside diameter pipeline in an active refinery. The pipeline chosen for testing in this case was carrying diesel fuel in an effort to contribute extraneous signals known to be caused by liquid within the pipe or tube under inspection. Signal (60) shown in FIG. 3 discloses, in addition to signal components (64), (66), and (68), which derive from the girth welds, a number of extraneous signal components (65), (67), and (69) are evidenced in the graph. It is anticipated that many of these extraneous signals are caused by the presence of the liquid in the pipe. However, identifying these signal components and distinguishing them from potential defects (such as signal component (70) in FIG. 3) is a complicated and difficult task if only the form of data displayed in FIG. 3 is utilized.

The methods of the present invention incorporate additional signal analysis steps into the existing techniques utilized in conjunction with magnetostrictive sensor NDE inspection systems. These steps involve taking the detected signals, such as those shown in FIG. 2b and FIG. 3, and transforming the detected signals into the time frequency domain. While a number of time frequency domain transformations are possible, techniques such as the short-time Fourier transform (STFT) have been found to be suitable for the proper identification of signal components under the conditions typically encountered in pipe and tubing inspection. FIG. 4 represents the time evolution of each frequency component of the detected signal shown in FIG. 2b. The gray scale utilized in FIG. 4 (as well as in FIG. 5) represents the relative amplitude of each frequency component in decibels.

In reference to the data shown in FIG. 4, signal (80) can be seen as comprising most of the same signal components shown and discriminated in FIG. 2b. These signal components, however, have additional characteristic features not present in FIG. 2b that permit distinguishing them from unknown features that are extraneous in nature. Specifically, transformed signal components (84), (86), and (88), each associated with the girth welds in the structure, appear as straight lines that are approximately parallel to the frequency axis in FIG. 4. Likewise, the transformed signals associated with the two known defects (92) (the notch) and (94) (the corrosion pit) also appear as straight lines parallel to the frequency axis.

Signal component (90) on the other hand, which is associated in time with signal component (58) shown in FIG. 2b, does not disclose characteristics similar to the girth weld and defect components of signal (80). This transformed extraneous signal between girth weld signal component (84) and girth weld signal component (86) appears as a curved line, which reveals that it is not from the longitudinal wave mode transmitted for inspection. According to known to dispersion properties of various wave modes, such an extraneous signal, associated with the curved line characteristic, may be identified as resulting from a flexural wave mode produced in the pipe wall as opposed to a defect signal. As indicated above, signal component (58) associated with this feature in FIG. 2b could easily have been identified as caused by a defect instead of the flexural wave mode produced in the pipe wall.

Appropriate analysis of the time frequency transform data shown in FIG. 4 permits the inspection process to easily distinguish signal component (90) from signal components (92) and (94) which genuinely represent defects of interest. Thus, in an automated system, computer analysis of the signal features shown in FIG. 4 would properly identify the curved structure (non-parallel to the frequency axis) of signal component (90) and would pass over that signal indication as not being indicative of a defect or anomaly demanding further inspection.

While a specific example of transformed signal data has been described showing a distinction between signal patterns that appear as lines parallel to the frequency axis and patterns that are curved, it is understood that other signal patterns may be predicted from the character of the incident wave and the known characteristics of the pipe under inspection. It is the a priori knowledge of the signal patterns that represent geometric or environmental characteristics of the system under inspection and the recognition of these patterns in the transformed data, that permits a discrimination of anomalous signal patterns.

Figure 5:
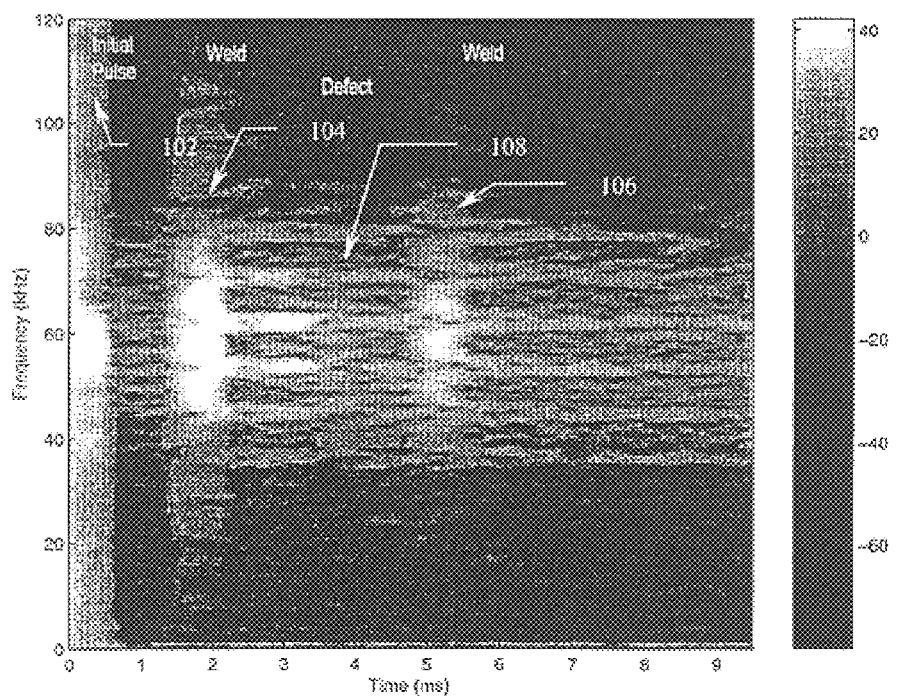
FIG. 5 is a graphical representation of the time evolution of each frequency component of the detected signal shown in FIG. 3 after a short-time Fourier transform of the data.

FIG. 5 represents the time evolution of each frequency component of the detected signal disclosed in FIG. 3. Again, as in FIG. 4, signal components (104) and (106) which derive from girth welds (corresponding to signal components (64) and (66) in FIG. 3) are recognizable as being approximately parallel to the frequency axis, as well as being branched into equally spaced regions. The feature most apparent in the data shown in FIG. 5 are the multiple lines running approximately parallel to the time axis. The branching in the lines parallel to the frequency axis and the lines parallel to the time axis are caused by the presence of liquid in the pipe, which changes the dispersion properties of the longitudinal wave mode in the pipe wall. From the representation of the data shown in FIG. 5, therefore, most of the extraneous signals (65), (67), and (69) shown in FIG. 3 can be identified as being caused by the effects of liquid in the pipe under inspection.

Close examination of the data displayed in FIG. 5 discloses a faint line running parallel to the frequency axis between the signal components representative of the two girth weld elements in the pipe. This signal component (108) can be distinguished from those signal components caused by the liquid in the pipe because of its distinctive orientation with respect to the frequency axis. In fact, signal component (108) represents defect (70) shown in FIG. 3 and maintains characteristic features in the transformed data shown in FIG. 5, similar to the characteristic features associated with girth weld signal components (104) and (106).

An automated system capable of processing the signal data shown in FIG. 5 could readily identify signal component (108) as being caused by a defect worthy of further investigation. Likewise, whereas signal components (65), (67), and (69) shown in FIG. 3 might be misinterpreted as being caused by defects, such signal components in FIG. 5 are readily identifiable as deriving from the liquid carried in the pipe.

Figure 6:
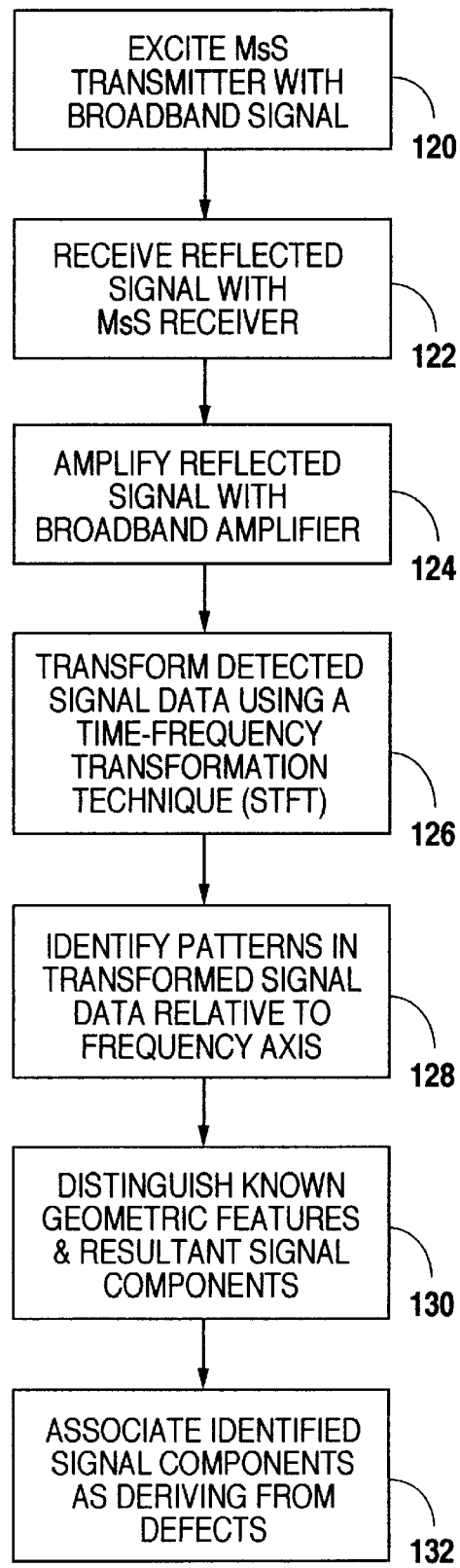
FIG. 6 is a flow chart showing the primary steps of the method of the present invention.

The method of the present invention is therefore generally disclosed in FIG. 6 wherein the steps of the process of analyzing the signal which improve upon earlier signal analysis techniques are disclosed. In FIG. 6 the process is initiated at step (120) by exciting the magnetostrictive sensor transmitter with a broadband interrogating signal. As indicated above, this is different from existing techniques that use a narrow band signal in order to avoid dispersion effects. In step (122) the process involves receiving a reflected signal with a magnetostrictive sensor receiver. In the preferred embodiment the magnetostrictive sensor may comprise the same structural elements as the magnetostrictive sensor transmitter. One of the advantages of the magnetostrictive sensor technique is the ability to interrogate and detect signals within an object under inspection from a single physical location. The same magnetostrictive sensor therefore may be utilized as both the transmitter and receiver under the method of the present invention.

The reflected signal received by the magnetostrictive sensor is then amplified at step (124) utilizing a broadband amplifier in order to maintain the broad frequency spectrum associated with the detected signal. It would be at this point that most existing analytical techniques would examine the signal received (a narrow bandwidth) and attempt to distinguish signal components representative of defects from other components associated with the geometry of the pipe under inspection. The present invention carries the broad bandwidth signal analysis technique further, however, and in step (126) transforms the detected signal data using a time-frequency transformation technique such as the short-time Fourier transformation. This step provides an additional dimension to the signal data that permits identification of signal components not present in the two-dimensional data established through simple signal time/amplitude detection.

The transformed data therefore discloses and permits in step (128) the identification of patterns that are specifically oriented with respect to the frequency axis in a plot of the data. Such patterns are identified as being associated either with geometric features within the pipe or tube under inspection or with defects of interest. In step (130) the a priori knowledge associated with the geometry of the pipe or tube under inspection is utilized to identify and distinguish those signal components known to be associated with geometric features. These signal components are then discarded as not being representative of defects or anomalies of interest.

Finally, in step (132) the method of the present invention categories identified signal components (those components identifiable by patterns in the transformed signal data relative to the frequency axis) which cannot be associated with known geometric features, as deriving from defects within the pipe under inspection. These defects can then be physically located by techniques well known in the art of quantifying the distance between signal components deriving from the defects and signal components deriving from known geometric features of the pipe under inspection. In this manner the method of the present invention can report inspection results that include the specific character of defects or anomalies of interest within the pipe structure as well as their physical location, for either further inspection or remedial action as necessary.

Although the methods of the present invention have been described in conjunction with the non-destructive evaluation of pipes, tubes and the like through the use of magnetostrictive sensors, it is anticipated that a variety of NDE techniques could benefit from the application of the analysis techniques described herein. Wherever a detected signal is made more complicated by extraneous effects unassociated with defects or anomalies of interest, the processes defined by the present invention could serve to distinguish such signal components in a manner that differentiates elements of interest from elements unassociated with defects or anomalies. It is anticipated that those skilled in the art of non-destructive evaluation technologies will recognize such various other applications of the methods of the present invention.

We claim:

1. A method for improved defect detection utilizing sensor based non-destructive evaluation techniques, comprising the steps of:
   exciting a sensor transmitter using a broadband frequency signal;
   receiving a reflected signal with a broadband sensor receiver over a period of time;
   amplifying said received signal with a broadband frequency signal amplifier;
   transforming said amplified signal using a time-frequency transformation technique;
   identifying patterns in said transformed signal relative to time and frequency axes for said transformed signal data;
   distinguishing identified patterns in said transformed signal data relative to said time and frequency axes known to be associated with geometric features for an object under inspection; and
   associating identified lines not distinguished as deriving from geometric features, with defects within said object under inspection.

2. The method of claim 1 wherein said sensor transmitter and said sensor receiver are each magnetostrictive based sensor devices.

3. The method of claim 1 wherein said sensor transmitter and said sensor receiver are positioned proximate to each other on said object under inspection.

4. The method of claim 2 wherein said sensor transmitter and said sensor receiver are functionally established by a single magnetostrictive based sensor device.

5. The method of claim 1 wherein said time-frequency transformation technique comprises a short-time Fourier transformation.

6. The method of claim 1 wherein said step of distinguishing identified patterns known to be associated with geometric features comprises establishing an a priori knowledge of said geometric features of said object under inspection and associating said identified patterns with said geometric features according to respective positions on the time axis for said transformed signal data.

7. The method of claim 6 further comprising the step of associating an a priori knowledge of signal amplitude for said identified patterns in said transformed signal data associated with said geometric features and comparing a measured signal amplitude for said geometric features with said a priori signal amplitude as confirmation of said step of distinguishing identified patterns as deriving from said geometric features.

8. A method for improved defect detection within a pipe or tube, utilizing a single magnetostrictive sensor, comprising the steps of:
   exciting said magnetostrictive sensor using a broadband frequency signal so as to generate a broadband spectrum of mechanical waves within said pipe or tube;
   receiving reflected mechanical waves over a period of time with said magnetostrictive sensor, said reflected mechanical waves deriving from and characterized by physical features of said pipe or tube and by an interaction of said pipe or tube with a fluid material contained within said pipe or tube, said magnetostrictive sensor generating an electrical signal having time varying amplitude and frequency characteristics corresponding to said reflected mechanical waves;
   amplifying said electrical signal with a broadband frequency signal amplifier;
   digitizing said amplified electrical signal;
   transforming said digitized signal using a short-time Fourier transformation technique;
   identifying patterns in said transformed signal relative to time and frequency axes for said transformed signal data;
   distinguishing at least one of said identified patterns relative to said time and frequency axes in said transformed signal data as associated with a geometric feature of said pipe or tube under inspection; and
   associating identified patterns not distinguished as associated with a geometric feature, with defects within said pipe or tube under inspection.

9. The method of claim 8 wherein said step of identifying patterns in said transformed signal relative to time and frequency axes comprises identifying lines in said transformed signal parallel to said frequency axis.

10. A method for improved defect detection with the use of sensor based NDE techniques, comprising the steps of:
    generating a broadband interrogating signal;
    receiving a reflected signal over a period of time;
    amplifying said received signal;
    applying a time-frequency transformation technique to said amplified signal;

identifying patterns in said transformed signal relative to time and frequency axes, said patterns not associated with geometric features of an object under inspection; and associating said identified patterns with defects within said object under inspection.

* * * * *